United States Patent [19]

Shafiee et al.

[11] Patent Number: 5,264,355

[45] Date of Patent: Nov. 23, 1993

[54] METHLATING ENZYME FROM STREPTOMYCES MA6858

[75] Inventors: Ali Shafiee, Westfield; Patricia M. Cameron, Titusville; David A. Boulton, Tinton Falls, all of N.J.; Louis Kaplan, New City, N.Y.; Haideh Motamedi, Westfield, N.J.

[73] Assignee: Merck & Co., Inc., Rahway, N.J.

[21] Appl. No.: 908,244

[22] Filed: Jul. 2, 1992

[51] Int. Cl.$^5$ ............................................. C12N 9/08
[52] U.S. Cl. ....................................................... 435/192
[58] Field of Search ........................................ 435/192

[56] References Cited

U.S. PATENT DOCUMENTS

| | | | |
|---|---|---|---|
| 4,894,366 | 1/1990 | Okuhara et al. | 514/63 |
| 4,929,611 | 5/1990 | Okuhara et al. | 514/183 |
| 4,956,352 | 9/1990 | Okuhara et al. | 514/63 |
| 4,975,372 | 12/1990 | Arison et al. | 540/456 |
| 4,981,792 | 1/1991 | Inamine et al. | 435/119 |
| 4,987,139 | 1/1991 | Chen et al. | 514/321 |
| 5,110,811 | 5/1992 | Okuhara et al. | 514/183 |
| 5,116,756 | 5/1992 | Dumont et al. | 435/253.5 |

FOREIGN PATENT DOCUMENTS

| | | |
|---|---|---|
| 0349061 | 1/1990 | European Pat. Off. . |
| 0353678 | 2/1990 | European Pat. Off. . |
| 0388152 | 9/1990 | European Pat. Off. . |
| 0388153 | 9/1990 | European Pat. Off. . |
| WO89/05304 | 6/1989 | World Int. Prop. O. . |

OTHER PUBLICATIONS

Tanaka, et al., *J. Am. Chem. Soc.*, 1987, 109 5031–5033.

*Primary Examiner*—Douglas W. Robinson
*Assistant Examiner*—Deborah Hung
*Attorney, Agent, or Firm*—Charles M. Caruso; J. Eric Thies

[57] ABSTRACT

Described is a new enzyme, 31-O-desmethyl-FK-506 O-methyltransferase (FKMT) and its N-terminal amino acid sequence. This enzyme can specifically and preferentially methylate the C-31 hydroxy group in 31-O-desmethyl FK-506/FR-900506 and other 31-O-desmethyl analogs of FK-506/FR-900506 and related compounds such as 31-O-desmethyl immunomycin type molecules, also designated FK-520 and FR-900520 by Fujisawa. The enzyme can be isolated from a FK-506 producing microorganism Streptomyces sp. (Merck Culture Collection No. MA 6858) ATCC No. 55098. Employing the enzyme in its active form, supplemented with $Mg^{+2}$ ion, in the presence of the methyl donor, S-adenosyl methionine (SAM), derivatives of 31-O-desmethyl FK-506, 31-O-desmethyl FK-520 and related 31-O-desmethyl compounds may be prepared.

3 Claims, No Drawings

METHLATING ENZYME FROM STREPTOMYCES MA6858

SUMMARY OF THE INVENTION

A new enzyme, FKMT, can be isolated in substantially pure form from a Streptomyces sp. (Merck Culture Collection No. MA 6858), ATCC No. 55098. The enzyme has a molecular weight of about 30,000 daltons, an isoelectric point 4.5, and is useful in being able to selectively methylate the C-31 hydroxy group in a 31-desmethyl FK-506 type molecule, in the presence of S-adenosyl methionine (SAM), a methyl donor agent.

By means of this enzyme, new C-31 methoxy FK-506 type compounds can be prepared for the first time and known C-31 methoxy compounds can be prepared by a novel methylation route specifically:

(1) starting with 13,31-bisdesmethylimmunomycin, described as L-683,756, the known C-13 desmethylimmunomycin, can be made by a novel route. The previously known route is by biotransformation on FK-900520 by the microorganism MA 6474 (ATCC No. 53771).

(2) starting with the known 15,31-bisdesmethylimmunomycin, known as L-686,292, the novel 15-desmethyl immunomycin can be made.

(3) starting with the known 13,15,31-trisdesmethylimmunomycin, L-687,795, the novel 13,15-bisdesmethylimmunomycin can be made.

By this invention there is provided a composition comprising a purified cell free enzyme, 31-O-desmethyl FK-506 O-methyltransferase (FKMT), having a molecular weight of about 30K daltons, as measured by SDS-PAGE, an isoelectric point (pI) of 4.5, and capable of catalyzing the C-31-O-methylation of a C-31 hydroxy containing FK-506 type molecule, in the presence of a methyl transfer agent, when supplemented with $Mg^{+2}$ ion.

Further provided is a process for methylating the C-31 hydroxy group in a C-31 hydroxy-containing FK-506 type molecule comprising the step of contacting the FK-506 type molecule with the methyl transfer agent S-adenosyl methionine in the presence of the FKMT enzyme described above, supplemented with the $Mg^{+2}$ ion, in an aqueous solvent therefor.

In addition, the disclosed N-terminal amino acid sequence may be utilized to locate the gene encoding similar enzymes.

BACKGROUND OF THE INVENTION

1. Field of the Invention

This invention relates to a new enzyme, 31-O-desmethyl FK-506 O-methyltransferase (FKMT) which can preferentially methylate the C-31 hydroxyl group in an FK-506 type molecule, e.g. 31-desmethylimmunomycin. Also disclosed are methods for the use of such compounds in a human host for treatment of autoimmune diseases, infectious diseases, the rejection of foreign organ transplants, reversible obstructive airways disease, inflammatory and hyperproliferative skin diseases, cutaneous manifestations of immunologically-mediated illnesses, male pattern alopecia and alopecia senilis.

2. Brief Description of Disclosures in the Art

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506,

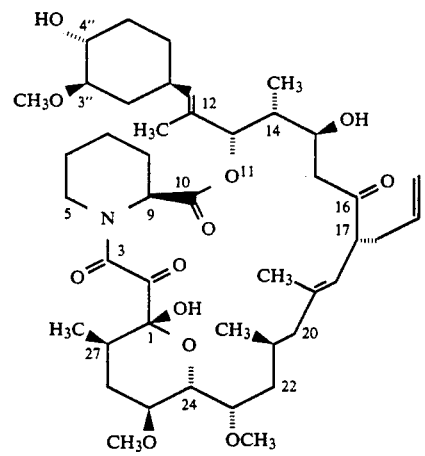

(17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.,* 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the suppression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), rheumatoid arthritis (C. Arita, et al., *Clinical exp. Immunol.,* 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al. *Lancet,* 1990, 336, 373–74), posterior uveitis (H. Kawashima, Invest. Ophthalmol. Vis. Sci., 1988, 29, 1265–71), hepatic injury associated with ischemia (M. Sakr, et al., *Life Sci.,* 1990, 47, 687–91) allergic encephalomyelitis (K, Deguchi, et al., *Brain Nerve,* 1990, 42, 391–97), glomerulonephritis (J. McCauley, et al., *Lancet,* 1990, 335, 674) systemic lupus erythematosus (K. Takabayashi, et al., *Clin. Immunol. Immunopathol.,* 1989, 51, 110-117), multidrug resistance (M. Naito, et al., *Cancer Chemother. Pharmacol.,* 1992, 29, 195–200), inflammation of mucosa and blood vessels (PCT Publication WO 91/17754), and idiopathic thrombocytopenic purpura and Basedow's disease (PCT Publication WO 91/19495).

DETAILED DESCRIPTION OF THE INVENTION

Streptomyes MA6858 is a gram positive filamentous bacterium which produces an immunosuppressant/antifungal compound known as FK-506. An enzyme, 31-O-desmethylFK-506 O-methyltransferase (FKMT), isolated from this organism specifically methylates 31-O-desmethyFK-506 and other 31-O-desmethylated analogues of FK-506 and related structure such as desmethylated immunomycins (FK-520). This enzyme has been purified, characterized and a portion of its N-terminal amino acid sequence has been determined.

In one embodiment, this invention is directed to a composition containing a purified cell free enzyme, FKMT, having a molecular weight of about 30K daltons, as measured by SDS-PAGE, an isoelectric point (pI) of 4.5, and capable of catalyzing the C-31 O-methylation of a C-31 hydroxy containing FK-506 type molecule, in the presence of a methyl transfer agent, when supplemented with $Mg^{+2}$ ion.

The enzyme can be isolated from a microorganism, Streptomyces sp. (MA 6858) ATCC No. 55098 and purified for enzymatic use by the procedure described in Example 3.

This enzyme in its purified state can be used to synthesize novel compounds with possible immunosuppressant/antifungal properties.

The sequence of this enzyme can also be used to locate and isolate the gene encoding it. Furthermore, in case of the clustering of the FK-506 biosynthetic genes, it can be used to detect and isolate other related genes.

The gene encoding this enzyme can be used to develop mutant strains with potential of producing new compounds.

Antibody produced against this enzyme can be used as a tool to screen for discovery of other producing cultures.

The methylating activity of this enzyme can be transferred to other organisms of interest through gene cloning technologies.

The enzyme is especially useful in a process for methylating the C-31 hydroxy group in a C-31 hydroxy-containing FK-506 type molecule involving the step of contacting the FK-506 type molecule with the methyl transfer agent, e.g., S-adenosyl methionine, in the presence of the FKMT enzyme described, supplemented with $Mg^{+2}$ ion, in an aqueous solvent therefor.

Generally, the process is conducted at a pH from about 7-9 and in the temperature range of about 25°–40° C.

The aqueous solvent system is generally a phosphate buffer of about pH=7-8.

The $Mg^{+2}$ ion is supplied as a soluble magnesium salt, e.g., magnesium chloride, magnesium sulfate, magnesium citrate, and the like.

Isolation and purification can be accomplished by conventional techniques including HPLC or reverse phase HPLC as described in the examples.

The enzyme is specific in methylating only the C-31 hydroxy group in an "FK-506 type molecule" and by that term is meant a molecule corresponding to the following Structure A, as described in PCT Publication 89/05304 (Jun. 15, 1989) and EP Publication 0,323,042 (Jul. 5, 1989) to Fisons:

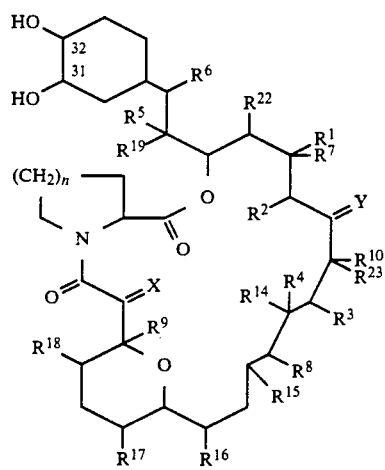

A wherein each vicinal pair of substituents:
$R^1$ and $R^2$; $R^3$ and $R^4$; $R^5$ and $R^6$; independently:
  a) represent two vicinal hydrogen atoms, or
  b) form a second bond between the vicinal carbon atoms to which they are attached; in addition to the significance above,
$R^2$ can represent an $C_1$-$C_{10}$ alkyl group;
$R^7$ represents H, OH or O-$C_1$-$C_{10}$ alkyl, or in conjunction with $R^1$ it may represent =O;
$R^8$ and $R^9$ independently represent H or OH;
$R^{10}$ represents H; $C_1$-$C_{10}$ alkyl, wherein said alkyl can be substituted by one or more hydroxyl groups;

$C_1$-$C_{10}$ alkenyl, which can be substituted by one or more hydroxyl groups, or $C_1$-$C_{10}$ alkyl substituted by =O;

X represents O, (H, OH), (H,H) or —$CH_2O$—;

Y represents O, (H, OH), (H,H), N—$NR^{11}R^{12}$ or N—$OR^{13}$ wherein, $R^{11}$ and $R^{12}$ independently represent H, $C_1$-$C_{10}$alkyl, $C_1$-$C_{10}$aryl or tosyl, and $R^{13}$, $R^{14}$, $R^{15}$, $R^{16}$, $R^{17}$, $R^{18}$, $R^{19}$, $R^{22}$ and $R^{23}$ independently represent H or $C_1$-$C_{10}$ alkyl;

n is 1,2, or 3;

in addition to their significances above, Y, $R^{10}$ and $R^{23}$, together with the carbon atoms to which they are attached, can represent a 5- or 6- membered N-, S- O-containing heterocyclic ring, which is saturated or unsaturated, and which can be substituted by one or more groups selected from $C_1$-$C_{10}$ alkyl, hydroxyl, $C_1$-$C_{10}$ alkyl substituted by one or more hydroxyl groups, O-$C_1$-$C_{10}$ alkyl, benzyl and —$CH_2Se(C_6H_5)$; provided that when X and Y both represent O; $R^9$ represents OH; $R^{14}$, $R^{15}$, $R^{16}$, $R^{17}$, $R^{18}$, $R^{19}$ and $R^{22}$ each represent methyl; $R^8$ and $R^{23}$ each represent H; [$R^3$ and $R^4$] and [$R^5$ and $R^6$] each represent a carbon-carbon bond; and pharmaceutically acceptable salts thereof, which includes acid addition salts of any amine groups present.

Also included are specific FK-506 structures corresponding to Structure B, which are published in U.S. Pat. No. 4,981,792, EPO Publication No. 0,349,049, EPO Publication No. 0,349,061 and EPO Publication No. 0,388,153:

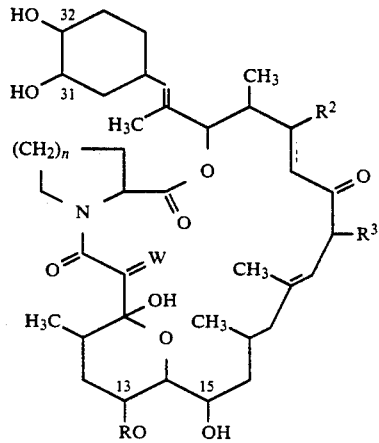

B wherein:

W represents O, (H, OH), or (H, H);

R is H, or $CH_3$;

$R^2$ is hydrogen, hydroxy or lower alkanoyloxy, $R^3$ is methyl, ethyl, propyl or allyl, n is an integer of 1 or 2, and the symbol of a line and dotted line is a single bond or a double bond, or a pharmaceutically acceptable basic salt thereof.

Specifically preferred are the compounds wherein: R is $CH_3$; $R^2$ is hydroxy; $R^3$ is ethyl; n is 2; and R is H; $R_2$ is hydroxy; $R_3$ is ethyl; n is 2.

The resultant C-31 methylated compounds can exhibit immunosuppressive activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay". The principle of this assay is to measure the proliferation of mouse T lymphocytes stimulated with the combination of ionomycin plus PMA. A positive sample in this assay will inhibit T-cell proliferation, as indicated by reduced tritiated thymidine uptake.

The process of the present invention involves the incubation and extraction of a Streptomyces sp. Merck Culture Collection No. MA 6858, ATCC No. 55098 to isolate the FKMT enzyme. The microorganism is currently on deposit with the American Type Culture Collection, 12301 Parklawn Drive in Rockville, Md. as ATCC No. 55098, and in the Merck Culture Collection in Rahway, N.J. as MA 6858. The physical characteristics and taxonomy, including morphological, cultural, biological and physiological characteristics of the microorganism, are briefly described hereinbelow.

The following is a general description of Streptomyces sp. strain MA 6858, ATCC No. 55098.

MA 6858

Observations of growth, general cultural characteristics and carbon source utilization were made in accordance with the methods of Shirling and Gottleib (Internat. J. System, Bacteriol. 16: 313-340). Chemical composition of the cells was determined using the methods of Lechavalier and Lechevalier (in Actinomycete Taxonomy, A. Kietz and D.W. Thayer, Ed. Society for Industrial Microbiology, 1980). Coloration of the culture was determined by comparison with color standards contained in the Inter-Society Color Council National Bureau of Standards Centroid Color Charts (U.S. Dept. of Commerce National Bureau of Standards supplement to NBS Circular 553, 1985). DNA-DNA homology of the strains was determined by the method described by Kurtzman, et al (Int. J. Syst. Bacteriol. 30: 208-216)

Source—MA 6858

This culture was isolated from the dung of white tailed deer, Poverty Creek Drainage, Montgomery County, Va.

Analysis of Cell Wall Composition—MA 6858

Peptidoglycan contains L-diaminopimelic acid. Whole cell carbohydrate analysis reveals glucose.

General Growth Characteristics

Good growth on yeast malt extract agar (YME), inorgaic salt starch agar, peptone iron agar and oatmeal agar. Fair growth on glycerol asparagine agar, Czapek's agar, trypticase soy agar and tap water agar supplemented with NZ-amine (Sheffield Chemical Co.) Sparse growth on tap water agar. Culture also grows in tryptone yeast extract broth. Culture grows at 27° C., but not at 37° C.

Colony Morphology—(on YME at 21 d)

Substrate mycelium is medium yellow brown. Aerial mycelium white. Spore mass, when present, is yellowish-white to light gray. Colonies are opaque, raised, with entire to lobate edges, rough textured and rubbery in consistency.

Micromorphology

Aerial mycelia (0.72 μm) arise in tufts from a substrate mycelium and are branched and flexous. Sclerotia are observed in the aerial mass when the culture is grown on either YME or oatmeal agar. In mature cultures, the aerial mycelium may terminate in flexous chains of spores at 7-28 d. Sporulation occurs in YME, inorganic salts-starch agar. Chains of spores are contained in a fibrous sheath and may be terminated by a "knot-like" structure at the apex. This characteristic is most notable on Czapek's agar and may appear as sporangia-like vesicles on immature cultures.

Miscellaneous Physiological Reactions

Culture produces $H_2S$ in peptone-iron agar but does not produce melanoid pigments. Carbon source utilization pattern is as follows: good utilization of β-D-lactose, D-mannose; moderate utilization of cellobiose, D-fructose, α-D-lactose; poor utilization of L-arabinose, D-mannitol, D-raffinose, L-rhamnose; no utilization of D-arabinose, inositol, D-maltose, sucrose, D-xylose, L-xylose.

DNA-DNA Homology

DNA-DNA homology studies were carried out with the three Streptomyces strains known to produce this class of compounds. (MA 6492 Streptomyces), *tsukubaensis*, FK-506 patent strain (See EPO 0,184,162); MA 6531 *Streptomyces hygroscopicus* subsp. *vakushimaensis*, FK-520/FK-523 patent strain (See EPO 0,184,162); MA 6475 *Streptomyces hygroscopicus* subsp. *ascomyceticus*, FK-520 producing strain (See U.S. Pat. No. 3,244,592). These experiments reveal that MA 6858 exhibits intermediate levels of homology with these three strains (MA 6492—54%, MA 6531—52%, MA 6475—48% at Tm-25C). In addition, reassociation kinetics show that the genome of MA 6858 is comparable in size to MA 6531 and MA 6475 but approximate 30% larger than that of MA 6492.

Diagnosis

Cell wall analysis reveals that MA 6858 has a type I cell wall and morphological studies reveal that the culture produces spores on straight to flexous sporophores which arise from the aerial mycelium. These are characteristics typical for strains of Streptomyces. A comparison of the phenotypic data of MA 6858 with that of the validly published species of Streptomyces in the literature shows that the strain has some similarity to *Streptomyces setonii* and *Streptomyces gougeroti*, but neither of those strains are reported to produce sclerotia, pseuduosporangia or other morphological structures in the aerial mycelia. In addition, both of those cultures are reported to utilize D-glucose whereas MA 6858 does so only sparingly. The following tables list the cultural characteristics and carbohydrate utilization pattern of MA 6858.

| Cultural Characteristics of Streptomyces sp. MA 6858 at 21 days | |
|---|---|
| Yeast Extract Malt Extract | |
| Amount of Growth: | Good |
| Aerial Mycelium and/or spores: | Aerial mycelium yellowish white (92 y White). Spores borne in straight chains. Sclerotia observed in aerial growth. |
| Soluble Pigments: | None |
| Reverse Color: | Medium yellow brown (76 m.yBr) |
| Glucose Asparagine | |
| Amount of Growth: | Fair |
| Aerial Mycelium and/or spores: | Aerial mycelium sparse, white (263 White). No sporulation evident. |
| Soluble Pigments: | None |
| Reverse Color: | light yellow brown (73 l.yBr) |
| Inorganic Salts Strach | |
| Amount of Growth: | Good |
| Aerial Mycelium and/or spores: | Aerial mycelium yellowish white (92 yWhite). Spores borne in long chains. Sclerotia also found. Starch vigorously hydrolyzed. |
| Soluble Pigments: | None |
| Reverse color: | Pale orange yellow (73 p.OY) |
| Oatmeal | |
| Amount of Growth: | Good |
| Aerial Mycelium and/or spores: | Aerial mycelium pale orange yellow (73 pOY). Spores borne in straight chains. Sclerotia present in aerial mass. |
| Soluble Pigments: | None |
| Reverse color: | Light orange yellow (70 l.OY) |
| Tap Water | |
| Amount of Growth: | Sparse |
| Aerial Mycelium and/or spores | No aerial growth observed. |
| Soluble Pigments: | None |
| Czapek | |
| Amount of Growth: | Fair |
| Aerial Mycelium and/or spores: | No aerial growth observed. |
| Soluble Pigments: | None |
| Peptone Iron | |
| Amount of Growth: | Good |
| Aerial Mycelium: | — |
| Soluble Pigments: | melanin negative, $H_2S$ positive |

| Carbohydrate utilization pattern of Streptomyces sp. MA6858 at 21 days | |
|---|---|
| Carbon Source | Utilization |
| D-arabinose | 0 |
| L-arabinose | 1 |
| cellobiose | 2 |
| D-fructose | 2 |
| inositol | 0 |
| α-D-lactose | 2 |
| β-D-lactose | 3 |
| D-maltose | 0 |
| D-mannitol | 1 |
| D-mannose | 3 |
| D-raffinose | 1 |
| L-rhamnose | 1 |
| sucrose | 0 |
| D-xylose | 0 |
| L-xylose | 0 |
| a-D-glucose (control) | 2 |

3 = good utilization,
2 = moderate utilization,
1 = poor utilization
0 = no utilization FKMT Enzyme Purification and Sequencing A six day old mycelial cells was prepared from a Streptomyces MA6858, a newly discovered FK-506 producer. Using an optimized O-methyltransferase assay as described in Example 6, an enzymatically functional cell-free preparation was obtained from these cells. This extract was therefore subjected to the various fractionation procedures which resulted in a highly purified active 31-O-desmethylFK-506 O-methyltransferase fraction (FKMT) from the Superose-12 column. This fraction had an elution volume similar to that of the standard carbonic anhydrase (CA) from the same column and showed a single band on the SDS-PAGE with mobility identical to CA. These results indicated that the FKMT enzyme isolated from the FK-506 producer is a single chain protein of 30,000 apparent molecular weight. A typical purification run afforded a highly purified FKMT enzyme. A sample of the purified FKMT thus prepared was submitted for the N-terminal amino acid analysis. This sample was sequenced after blotting to PVDF (polyvinylidene fluoride) membrane to give the following N-terminal amino acid sequence (SEQ ID NO:1:):

Ser Asp Val Val Glu Thr Leu Arg Leu Pro Asn Gly Ala Thr
1               5                    10

Val Ala His Val Asn Ala Gly Glu Ala Gln Phe Leu Tyr Arg Glu Ile
15              20                  25                  30

Phe Thr Asp Arg Xaa Tyr Leu Arg His
            35

Properties of the FKMT Enzyme

This enzyme, is SAM dependent and has requirement for $Mg^{+2}$ with optimum concentration of 4 mM. SAM concentration up to 550 uM did not show any substrate inhibition, therefore, 220 uM of SAM was regularly used in the standard assay. Similarly, there was no substrate inhibition observed above 50 uM when substrate A was used as variable in the presence of fixed concentration of SAM (220 µM). The temperature effect on the methylation reaction was examined at 0°, 22°, 24°, 34°, 37°, and 44° C. The optimum temperature for the reaction was determined to be at 34° C. Above this temperature there was a problem with substrate decomposition. Under the established incubation condition in which 31 uM of substrate A and 220 uM of SAM were used, the rate of the methylation reaction was linear up to 35 min with protein concentration up to 100 ug.

FKMT Kinetic Analysis

For the kinetic studies, a preparation of the FKMT enzyme which had been purified through the second MonoQ column chromatography was used. Under conditions for the initial velocity measurement, apparent Km and Vmax were determined for 31-O-desmethyFK-506 (substrate A) at one saturating concentration of SAM (220 mM). The graphically determined kinetic parameters indicate values of 2.33 nmole/mg/min and 23.21 uM for the apparent Vmax and Km, respectively.

Substrate Specificity of FKMT

Substrate specificity studies demonstrated that the DIMT enzyme can only methylate 31-O-position of the various desmethylated compounds. This specificity was therefore exploited to produce two novel desmethylated forms of immunomycin, namely, 15-O-desmethyl-and 13, 15-O-bis-desmethylimmunomycins. Based on this experience, various 31-O-desmethylated derivatives of the immunomycin were examined for 31-O-methylation using the FKMT enzyme that had been isolated from the Streptomyces sp. MA6858, an FK-506 producer. Among all the analogues tested, only those structures with free hydroxyl at 32-O-position could be methylated.

The following examples are given for the purpose of illustrating the present invention and should not be construed as being limitations on the scope or spirit of the instant invention.

EXAMPLE 1

MA 6858 Culture Isolation

A sample of a fermentation broth was streaked for isolation onto AK agar medium and then incubated at 28° C. The agar composition is as follows:

| AK Agar Medium | |
|---|---|
| Agar | 20.0 g |
| Dextrose | 10.0 g |
| Asparagine | 1.0 g |
| $K_2HPO_4$ | 0.1 g |
| $MgSO_4.7H_2O$ | 0.5 g |
| Yeast Extract | 0.5 g |
| Trace Elements* | 10 ml |
| Distilled $H_2O$ | 1000 ml |
| pH 7.2 | |
| *Trace Elements | |
| $FeSO_4.7H_2O$ | 1000 mg |
| $MnSO_4.4H_2O$ | 1000 mg |
| $CuCl_2.2H_2O$ | 25 mg |
| $CaCl_2$ | 100 mg |
| $H_3BO_3$ | 56 mg |
| $(NH_4)_6Mo_7O_{24}.4H_2O$ | 19 mg |
| $ZnSO_4.7H_2$ | 200 mg |
| 0.1 N HCl | 1000 ml |

After 7-10 days incubation, a morphologically distinct colony-type was observed to have grown on the agar medium. Microscopic observation of this colony-type showed it to be a Streptomyces. The Streptomyces was isolated into pure culture and fermented. The culture was deposited in the Merck Culture Collection with accession number MA 6858.

Fermentation

A seed culture was produced by inoculating 50 ml of BaSa Seed Medium (described below) in a 250 ml triple baffled erlenmeyer flask with 2-4 ml of a slant suspension of MA 6858. The culture vessel was incubated at 27° C. and shaken at 220 rpm under 85% humidity. After 48 hours incubation, the seed culture was sufficiently grown to be used as an inoculum.

The production medium FKP-1A (described below) (44 ml per 250 ml unbaffled erlenmeyer flask) was inoculated with 2 ml of seed culture and incubated under the temperature, shaker flask and humidity conditions described previously for 4-7 days. At daily intervals during incubation, a sample (2 ml) was aseptically removed from the production culture and examined for the production of FK-506. i.e. immunosuppressive (IP) activity. Whole flasks were harvested following 4 or 7 days fermentation. Under standard fermentation conditions as described above, the highest titer of FK-506 was obtained after 5-6 days.

| BaSa Seed Medium | |
|---|---|
| NaCl (12.5% solution) | 4 ml |
| $MgSO_4.7H_2O$ (12.5% solution) | 4 ml |
| $FeSO_4.7H_2O$ | 0.25 g |
| $MnSO_4.7H_2O$ (0.5% solution) | 1 ml |
| $Cacl_2.2H_2O$ (2% solution) | 1 ml |
| $ZnSO_4.7H_2O$ (1% solution) | 1 ml |
| $KNO_3$ | 1 g |
| HyCase SF | 20 g |
| Yeast Extract | 20 g |
| Glucose | 20 g |
| in total volume of | 1000 ml |
| (pH = 7.0) | |
| Production medium, Fkp-1A | |
| Soluble Starch | 20 g |
| Corn Steep Liquor | 15 g |
| Glucose | 10 g |
| Dried Yeast | 6 g |
| Pharmamedia | 2 g |
| $CaCO_3$ | 1 g |
| MOPS | 10 g |

EXAMPLE 2

Bacterial growth and mycelium preparation

Frozen vegetative mycelium of Streptomyces MA6858 was cultured in the seed and fermentation media. The mycelium was harvested at 141 hours and washed three times with phosphate buffer, pH=7.5, containing 0.5M KCl and finally with plain buffer. Washed mycelium was used for the preparation of the cell-free extract.

EXAMPLE 3

Isolation of the 31-O-desmethyl FK-506 O:methyltransferase (FKMT)

All of the procedures and sample manipulations were carried out on ice or in the cold room. Functional cell-free extract was prepared as follows: washed mycelium was suspended in 50 mM phosphate buffer, pH 7.5 containing 1 mM PMSF/10% ethanol (Buffer A) and 1 mg/ml of lysozyme. The resulting suspension was stirred overnight and centrifuged at 15000 rpm for 30 mins. The pellet thus obtained was broken by passage through a French press. The cell homogenate was centrifuged as before and the supernatants were combined and re-centrifuged at 105K×g for 45 mins. Cell-free extract thus prepared was brought to 1% streptomycin sulfate, stirred for 30 min. and centrifuged at 105K×g. After 45 min. centrifugation, the supernatant was recovered and brought to 30% ammonium sulfate saturation and stirred for 30 min. The resulting suspension was centrifuged at 15000 rpm for 20 min. and the supernatant was then brought to 60% ammonium sulfate saturation. After 30 min. stirring, the resulting suspension was centrifuged at 15000 rpm for 20 min., and the pellet was recovered. This pellet was dissolved in buffer A and after another round of centrifugation was dialysed against the same buffer. The dialysed sample was then applied on a column containing DEAE-Sepharose. This column was developed with buffer A containing a linear gradient of KCl from zero to 1 molar. Five milliliter fractions were collected and examined for FKMT enzyme activity. Fractions showing the FKMT activity were pooled, concentrated and dialysed against buffer A and subjected to MonoQ HR10/10 column using Pharmacia FPLC system. This column was developed similar to that of the DEAE-Sepharose column except that reservoir B contained 0.5M KCl and the gradient was run for 95 min. One milliliter fractions with a flow rate of 60 ml/hr were collected from this MonoQ column and enzyme assays were carried out. Active fractions were pooled and, after preparation and dialysis against starter buffer, was applied on the Pharmacia MonoP HR5/20 chromatofocusing column. This column was developed with a solution of a polybuffer with pH interval of 7 to 4. One milliliter fractions with a flow rate of 30 ml/hr were collected and enzyme assays were carried out on various fractions. Fractions showing improved specific activity as judged by the results of the enzyme assays and SDS-PAGE were pooled together and after necessary preparation was subjected to an analytical MonoQ HR5/5 column. This column was run under similar chromatographic conditions as described for the preparative MonoQ column and fractions were collected. Active fractions showing improved specific activity were pooled together and concentrated using CF-25 centriflo membrane cone (Amicon). The resulting concentrated fraction was applied on a calibrated Superose-12 column and the column was developed with buffer A containing 150 mM NaCl with a flow rate of 18 ml/hr. Fractions of 0.3 ml in size were collected and each examined for the FKMT activity and for purity and immunoreactivity by SDS-PAGE, and Western blotting.

EXAMPLE 4

N-Terminal Amino Acid Sequence Analysis

N-terminal amino acid sequence analysis was carried out as described below. The sample was concentrated by ultrafiltration on a 10,000 NMWL cutoff membrane (Millipore). The entire sample was then electrophoresed on a single lane of a 10% Tricine SDS gel (Novex). The proteins were electroblotted to Immobilon-P (Millipore) and stained with amido black in 50% methanol. The predominant band (30,000 MW) was excised and sequenced by automated gas-phase Edman degradation (Porton 2090 sequencer) according to the manufacturer's instructions.

EXAMPLE 5

Preparation of 31-O-desmethylFK-506 substrate

This material (substrate A) was prepared according to the following biotransformation procedures. A 1 ml. culture of Actinoplanes (ATCC No. 53771) was inoculated in 50 ml. of seed medium (see below) and the culture was incubated overnight at 27° C. with 220 rpm agitation. The resulting seed culture was transferred into 50 ml of biotransformation medium (see below) containing 5 mg of FK-506. This culture was incubated as above and then harvested after 18 hours and worked-up for the isolation and purification of 31-O-desmethyl FK-506 which was used as substrate. 31-O-desmethyl-immunomycin can be used as an alternative substrate during the purification of FKMT.

| Seed Medium | |
|---|---|
| Dextrin | 10.0 g |
| Glucose | 1.0 g |
| Beef Extract | 3.0 g |
| Ardamine PH | 5.0 g |
| N-Z Amine Type E | 5.0 g |
| $MgSO_4.7H_2O$ | 0.05 g |
| $KH_2PO_4$ | 0.37 g |
| $CaCO_3$ | 0.5 g |
| (pH = 7.1) | |
| Biotransformation Medium | |
| Glucose | 10 g |
| Hy-case SF | 2 g |
| Beef Extract | 1 g |
| Corn Steep Liquor | 3 g |
| (pH = 7.0) | |

EXAMPLE 6

S-Adenosyl-L-methionine: 31-O-Desmethyl-FK-506-O-Methyltransferase (FKMT) Assay and Product Identification The assay was carried out in 1 ml. mixture containing 0.025 mM 31-desmethyl FK-506, 4 mM $MgSO_4$ and different quantities of the enzyme source in 50 mM phosphate buffer, pH 7.5. Reaction was initiated by the addition of 1 nmole of $^{14}$C-SAM (S-adenosyl-L-[methyl-14C] methionine) with the specific activity of 46 mCi/mmole. Incubation of the complete mixture was carried out at 34° C. for 20 mins. and the reaction was terminated by the addition of ethyl acetate. Product of the reaction was extracted with 2 ml. of ethyl acetate and 1 ml. of the extract was used for TLC and HPLC analysis. For the analysis of the radioactive reaction product (FK-506), the ethyl acetate extract was spiked with the standard FK-506 and subjected to the silica gel TLC with plastic support. The plastic sheet was developed in chloroform:methanol (9:1) and area showing standard FK-506 under UV-light was cut and the radioactivity in the cut-strip was measured and the amount of the product formed was calculated.

EXAMPLE 7

General Methods

Polyacrylamide gel electrophoresis (PAGE), molecular weight determination, Western blot analysis and protein determination were all carried out according to the following procedures.

The molecular weight of the native enzyme was determined by gel filtration chromatography on Superose-12 column. Column was equilibrated and run in buffer L containing 150 mM NaCl and with a flow rate of 18 ml./hour. The apparent molecular weight of the denatured enzyme was estimated by SDS-PAGE according to Laemmli (*Nature* (London) Vol. 227, pp. 680-685 (1970)). In both gel filtration and SDS-PAGE, bovine serum albumin (Mr=66000), egg albumin (Mr=45000), carbonic anhydrase (Mr=31000), and cytochrome C (Mr=12400) were used as standards. Isoelectric point of the purified enzyme was estimated by both chromatofocusing on a Pharmacia MonoP HR5/20 column with a pH interval of 7-4 and calibrated isoelectric focusing-PAGE having interval of 3-9.

Native-PAGE was carried out according to Laemmli, supra, with the elimination of the SDS from the buffer system. Protein concentration was determined by the Bio-Rad protein assay system with bovine serum albumin as standard.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A purified enzyme, 31-O-desmethylFK-506 O-methyltransferase, having a molecular weight of about 30K daltons, as measured by SDS-PAGE, an isoelectric point (PI) of 4.5, and capable of catalyzing the C-31 O-methylation of a C-31 hydroxy containing FK-506 type molecule, in the presence of a methyl transfer agent, when supplemented with $Mg^{+2}$ ion.

2. The enzyme of claim 1 wherein the N-terminal amino acid sequence comprises the amino acid sequence (SEQ ID NO: 1:) which is:

Ser Asp Val Val Glu Thr Leu Arg Leu Pro Asn Gly Ala Thr
1               5                   10

Val Ala His Val Asn Ala Gly Glu Ala Gln Phe Leu Tyr Arg Glu Ile
15              20              25              30

Phe Thr Asp Arg Xaa Tyr Leu Arg His.
            35

3. A composition comprising a cell-free extract of purified enzyme, 31-O-desmethylFK-506 O-methyltransferase, having a molecular weight of about 30K daltons, as measured by SDS-PAGE, an isoelectric point (PI) of 4.5, and capable of catalyzing the C-31 O-methylation of a C-31 hydroxy containing FK-506 type molecule, in the presence of a methyl transfer agent, when supplemented with $Mg^{+2}$ ion in combination with a carrier or solvent.

* * * * *

SEQUENCE LISTING
(1) GENERAL INFORMATION:
  (i) APPLICANTS: Shafiee, Al,
      Boulton, D. A.,
      Cameron, P. M.,
      Kaplan, L.,
      Motamedi, H.
  (ii) TITLE OF INVENTION: METHYLATING ENZYME FROM STREPTOMYCES MA6858
  (iii) NUMBER OF SEQUENCES: 1
  (iv) CORRESPONDENCE ADDRESS:
      (A) ADDRESSEE: Merck & Co., Inc.
      (B) STREET: P.O. Box 2000
      (C) CITY: Rahway -continued (D) STATE: NJ
  (E) COUNTRY: US
  (F) ZIP: 07065
  (v) COMPUTER READABLE FORM:
      (A) MEDIUM TYPE: Floppy disk
      (B) COMPUTER: IBM PC compatible
      (C) OPERATING SYSTEM: PC-DOS/MS-DOS
      (D) SOFTWARE: PatentIn Release #1.0, Version #1.25
  (vi) CURRENT APPLICATION DATA:
      (A) APPLICATION NUMBER:
      (B) FILING DATE: 02-JUL-1992
      (C) CLASSIFICATION:
  (viii) ATTORNEY/AGENT INFORMATION:
      (A) NAME: Thies, J. Eric
      (B) REGISTRATION NUMBER: 35,382
      (C) REFERENCE/DOCKET NUMBER: 18708
  (ix) TELECOMMUNICATION INFORMATION:
      (A) TELEPHONE: (908) 594-3904
      (B) TELEFAX: (908) 594-4720
      (C) TELEX: 138825
(2) INFORMATION FOR SEQ ID NO:1:
  (i) SEQUENCE CHARACTERISTICS:
      (A) LENGTH: 39 amino acids
      (B) TYPE: amino acid
      (C) STRANDEDNESS: single
      (D) TOPOLOGY: linear
  (ii) MOLECULE TYPE: peptide
  (v) FRAGMENT TYPE: N-terminal
  (xi) SEQUENCE DESCRIPTION: SEQ ID NO:1:
Ser Asp Val Val Glu Thr Leu Arg Leu Pro Asn Gly Ala Thr
1               5                   10
Val Ala His Val Asn Ala Gly Glu Ala Gln Phe Leu Tyr Arg Glu Ile
15              20              25              30
Phe Thr Asp Arg Xaa Tyr Leu Arg His
            35